(12) United States Patent
Renga

(10) Patent No.: US 9,353,060 B2
(45) Date of Patent: May 31, 2016

(54) PROCESS FOR THE PREPARATION OF 3-HYDROXYPICOLINIC ACIDS

(71) Applicant: DOW AGROSCIENCES LLC, Indianapolis, IN (US)

(72) Inventor: James M. Renga, Spokane, WA (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/793,251

(22) Filed: Jul. 7, 2015

(65) Prior Publication Data

US 2016/0009647 A1  Jan. 14, 2016

Related U.S. Application Data

(60) Provisional application No. 62/021,868, filed on Jul. 8, 2014.

(51) Int. Cl.
 *C07D 213/803* (2006.01)
 *C07D 307/54* (2006.01)

(52) U.S. Cl.
 CPC .......... *C07D 213/803* (2013.01); *C07D 307/54* (2013.01)

(58) Field of Classification Search
 None
 See application file for complete search history.

(56) References Cited

U.S. PATENT DOCUMENTS

| | | | |
|---|---|---|---|
| 4,406,905 A | 9/1983 | Zahner et al. | |
| 4,506,084 A | 3/1985 | Kay et al. | |
| 6,355,660 B1 | 3/2002 | Ricks | |
| 6,521,622 B1 * | 2/2003 | Ricks | A01N 43/40 514/252.01 |
| 6,706,740 B2 | 3/2004 | Ricks | |
| 6,743,804 B2 * | 6/2004 | Giardina | A61K 31/47 514/311 |
| 6,861,390 B2 | 3/2005 | Meyer | |
| 6,927,225 B2 | 8/2005 | Ricks | |
| 7,034,035 B2 | 4/2006 | Ricks | |
| 7,183,278 B1 | 2/2007 | Imamura | |
| 7,250,389 B1 | 7/2007 | Sakanaka | |
| 8,785,479 B2 | 7/2014 | Meyer | |
| 8,835,462 B2 | 9/2014 | Meyer | |
| 8,883,811 B2 | 11/2014 | Owen | |
| 2002/0177578 A1 | 11/2002 | Ricks | |
| 2003/0018012 A1 | 1/2003 | Ricks | |
| 2003/0018052 A1 | 1/2003 | Ricks | |
| 2003/0022902 A1 | 1/2003 | Ricks | |
| 2004/0034025 A1 | 2/2004 | Ricks | |
| 2004/0048864 A1 | 3/2004 | Ricks | |
| 2004/0171838 A1 | 9/2004 | Meyer | |
| 2004/0186296 A1 | 9/2004 | Nyaz | |
| 2004/0192924 A1 | 9/2004 | Meyer et al. | |
| 2005/0176767 A1 | 8/2005 | Kong et al. | |
| 2005/0239873 A1 | 10/2005 | Hockenbery | |
| 2007/0060579 A1 | 3/2007 | Wachendorff-Neumann | |
| 2007/0066629 A1 | 3/2007 | Blasco | |
| 2009/0306142 A1 | 12/2009 | Carson | |
| 2011/0053966 A1 | 3/2011 | Klittich et al. | |
| 2011/0082162 A1 | 4/2011 | Lorsbach et al. | |
| 2012/0245031 A1 | 9/2012 | Gewehr et al. | |
| 2013/0296371 A1 | 11/2013 | Meyer | |
| 2013/0296373 A1 | 11/2013 | Meyer et al. | |
| 2014/0128411 A1 | 5/2014 | Ogawa et al. | |
| 2014/0187587 A1 | 7/2014 | Ouimette | |
| 2014/0187588 A1 | 7/2014 | Lalonde | |
| 2014/0275171 A1 | 9/2014 | Meyer | |
| 2015/0065529 A1 | 3/2015 | Owen | |

FOREIGN PATENT DOCUMENTS

| | | |
|---|---|---|
| EP | 1516874 | 3/2005 |
| WO | 01/14339 | 3/2001 |
| WO | 2009040397 | 9/2008 |
| WO | 2012/070015 | 5/2012 |

OTHER PUBLICATIONS

Y.Usuki, et al. Journal of Antibiotics, vol. 55, No. 6, Jun. 2002, pp. 607-610.
Gisi, U. The American Phytopathological Society, vol. 86, No. 11, 1996, P. 1273-79.
Anonymous, Synergistic Fungicidal Composition of Heterocyclic Aromatic Amides and Triazoles, IP.Com, Electronic Publication, 2004, 11 pages.
Anonymous, Synergistic Fungicidal Composition of Heterocyclic Aromatic Amides and Triazoles, IP.Com Journal, IP.Com, Inc., West Henrietta, NY, US, Dated Jul. 2004, 10 pages.
K. Tani, et al., Journal of Antibiotics, vol. 55, No. 3, Mar. 2002, pp. 315-321.
Z. Hu, et al, Synthesis of Novel Analogues of Antimycin A3, Tetrahedron Letters 49 (2008) pp. 5192-5195.
Kissling, Crop Protection pipeline value jumps to € 2.4 billion. BASF. Mar. 11, 2010, pp. 1-4, [retrieved on Feb. 4, 2014]. Retrieved from the Internet: <URL: http://www.agro.basf.com/agr/AP-Internet/en/content/news_room/news/basf-crop-protection-pipaline-value>.
BASF new fungicide Xemium got full approval in EU. AgroNews. Jul. 18, 2012 [retrieved on 1-20 Feb. 4, 2014). Retrieved from the Internet: <URL: http://news.agropages.com/News/NewsDetail—7386.htm>.
Demir, A.S., et al, "An asymmetric sythesis of both enantiomers of 2,2,2-trifluror-1-furan-2-yl-ethylamine and 3,3,3-trifluoroalanine from 2,2,2-trifluroro-1-furan-2-yl-ethanone," Tetrahedron: Asymmetry 12 (2001) 2309-2313.
Baruah, P.K, et al., "Synthesis, anticonvulsant activity, and neuropathic pain attenuating activity of N-benzyl 2-amino-2-(hetero)aromatic acetamides," Bioorganic & Medicinal Chemistry 20, (2012) 3551-3564.
Clauson-Kass, N., et al, "Preparation of Derivatives of 3-Hydroxypicolinic Acid from Furfural", Acta Chemica Scandinavica, 1965, vol. 199, pp. 1147-1152.
International Searching Authority, Written Opinion for PCT/US15/39411, dated Oct. 6, 2015, 7 pages.

(Continued)

*Primary Examiner* — Zinna Northington Davis
(74) *Attorney, Agent, or Firm* — C. W. Arnett; Faegre Baker Daniels LLP

(57) ABSTRACT

4,6-Dibromo-3-hydroxypicolinate esters are prepared from furan-2-yl aminoacetates in one chemical step by use of a bromination-rearrangement reaction.

11 Claims, No Drawings

(56) References Cited

OTHER PUBLICATIONS

International Searching Authority, International Search Report for PCT/US15/39411, dated Oct. 6, 2015, 3 pages.

Guo-Qiang Shi, "delta, epsilon-Unsaturated beta,beta-Difluoro-alpha-keto Esters: Novel Synthesis and Utility as Precursors of beta,beta-Difluoro-alpha-amino Acids," Journal Organic Chemistry, 1995, 60 pp. 6289-6295.

PUBCHEM-CID-11435037 Create Date: Oct. 26, 2006, 10 pages.

Goldberg, AA, et al., "254. Synthesis of Omega-Aminoalkyl Cyanides" Journal of the Chemical Society, 1947, pp. 1369-1371.

* cited by examiner

PROCESS FOR THE PREPARATION OF 3-HYDROXYPICOLINIC ACIDS

CROSS REFERENCE TO RELATED APPLICATIONS

This application claims the benefit of U.S. Provisional Patent Application Ser. No. 62/021,868 filed Jul. 8, 2014, which is expressly incorporated by reference herein

FIELD

The present disclosure concerns a process for the preparation of 4-alkoxy-3-hydroxypicolinic acids. More particularly, the present disclosure concerns a process for the preparation of 4-alkoxy-3-hydroxypicolinic acids from 2-substituted furans.

BACKGROUND

U.S. Pat. No. 6,521,622 B1 and U.S. Application Ser. No. 61/747,723 and Ser. No. 14/142,183, the disclosures of which are hereby incorporated by reference in their entireties, describe inter alia certain heterocyclic aromatic amide compounds of general Formula

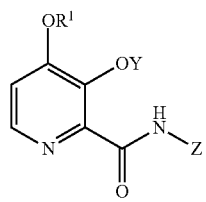

and their use as fungicides.

These disclosures also describe the preparation of 4-alkoxy-3-hydroxypicolinic acids as key intermediates in the preparation of these heterocyclic aromatic amides. It would therefore be useful to have efficient and scalable process routes to 4-alkoxy-3-hydroxypicolinic acids from inexpensive raw materials.

SUMMARY

The present disclosure concerns a process for the preparation of a compound of Formula A

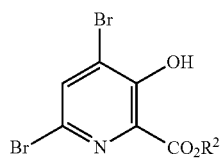

wherein $R^2$ is a $C_1$-$C_4$ alkyl.

The compound of Formula A is useful in processes to prepare 4-alkoxy-3-hydroxypicolinic acids of Formula

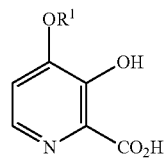

wherein $R^1$ is a $C_1$-$C_3$ alkyl.

The compound of Formula A is prepared in a process that comprises the following steps:

a) creating a mixture by adding a brominating agent, a base and water to the compound of Formula B

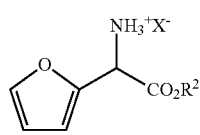

wherein X is Cl or Br, and $R^2$ is a $C_1$-$C_4$ alkyl; and b) isolating the compound of Formula A from the mixture.

The compound of Formula B is prepared in a process that comprises the following steps:

a) creating a first mixture by combining together an O-alkylhydroxylamine hydrohalide salt of the Formula I

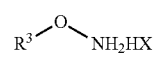

wherein X is Cl or Br, and $R^3$ is a $C_1$-$C_4$ alkyl; a base, a solvent and the compound of Formula C;

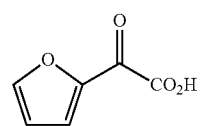

b) isolating a compound of Formula D from the first mixture

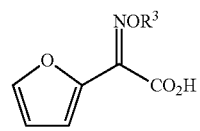

wherein $R^3$ is a $C_1$-$C_4$ alkyl;

c) mixing the compound of Formula D with an alcohol and an acid compound or acid forming compound and then heating to form a second mixture; and d) isolating a compound of Formula E from the second mixture

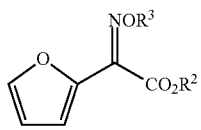

wherein $R^2$ and $R^3$ are independently a $C_1$-$C_4$ alkyl;

e) adding a reducing agent to the compound of Formula E to form a third mixture;

f) isolating a compound of Formula F from the third mixture.

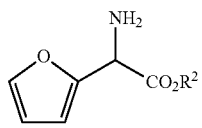

wherein $R^2$ is a $C_1$-$C_4$ alkyl;

g) adding a mineral acid to the compound of Formula F to form a fourth mixture; and h) isolating the compound of Formula B from the fourth mixture.

The compound of Formula B may also be prepared in a process that comprises the following steps:

a) creating a first mixture by combining together furan, a Lewis acid and the compound of Formula G

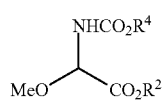

wherein $R^2$ is a $C_1$-$C_4$ alkyl and $R^4$ is an acid cleavable group selected from an allyl, a benzyl or a substituted allyl or benzyl group;

b) isolating a compound of Formula H from the first mixture

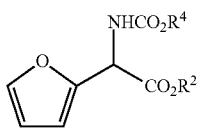

wherein $R^2$ and $R^4$ are as defined in a);

c) adding a mineral acid to the compound of Formula H to form a second mixture; and d) isolating the compound of Formula B from the second mixture. In some embodiments the Lewis acid used in the process is boron trifluoride etherate. In some embodiments the acid cleavable group is a benzyl group. And in some embodiments the strong acid used in the process is at least one acid selected from the group consisting of hydrochloric acid and hydrobromic acid.

Another aspect of the present disclosure is a novel intermediate produced in the present process, viz., the compound consisting of:

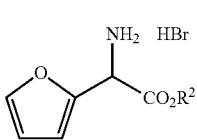

wherein $R^2$ is a $C_1$-$C_4$ alkyl.

DETAILED DESCRIPTION

The terms "isolate," "isolating," or "isolation" as used herein mean to partially or completely remove the desired product from the other components of a finished chemical process mixture using standard methods such as, but not limited to, filtration, extraction, distillation, crystallization, centrifugation, trituration, liquid-liquid phase separation or other methods known to those of ordinary skill in the art. The isolated product may have a purity that ranges from ≤50% to ≥50%, and may be purified to a higher purity level using standard purification methods. The isolated product may also be used in a subsequent process step with or without purification.

Cyano(furan-2-yl)methanaminium halide salts of Formula 1a have been prepared and used as intermediates in the preparation of 3-hydroxypicolinonitriles and 3-hydroxy-picolinoamides of Formula 1b as described in *Acta Chem. Scand.* 19 (1965), pg. 1147-1152,

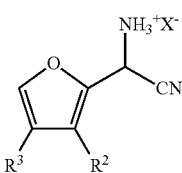

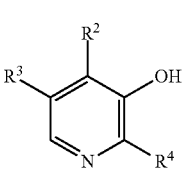

wherein X is Cl, $R^2$ is H or methyl, $R^3$ is H or 2-propyl, and $R^4$ is CN or $C(O)NH_2$.

A. Preparation of Compound of Formula A

In the process described herein, 4,6-dibromo-3-hydroxypicolinate esters of Formula A are prepared from alkyl 2-amino-2-(furan-2-yl)acetate hydrohalide salts of Formula B in one chemical step by use of a bromination-rearrangement reaction. The starting furan compound of Formula B, as either the HCl or HBr salt and where $R^2$ represents a $C_1$-$C_4$ alkyl, is treated with a suitable brominating agent such as bromine, 1,3-dibromo-5,5-dimethylhydantoin or N-bromosuccinimide. The reaction is preferably conducted using about 4 molar equivalents of bromine. It may be convenient to use an excess of the brominating agent such as a 5%,

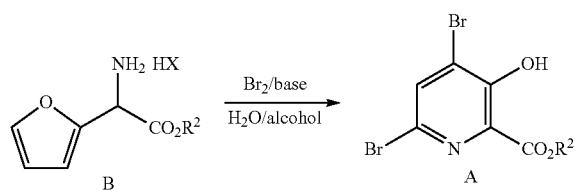

10% or 15% molar excess, to insure the reaction proceeds to completion. A base is used in the reaction and may be selected from sodium acetate or potassium acetate and the like. The reaction is preferably carried out in a protic solvent or reaction medium such as water, or mixtures of water and an alcohol such as, methanol or ethanol. The temperature at which the reaction is conducted is between about 0° C. and about 10° C., preferably between about 0° C. and about 5° C. Upon completion of the addition of the brominating agent, the reaction mixture is allowed to warm to room temperature and stir there for 15-48 hours. After the reaction is complete, the desired product is recovered by employing standard isolation and purification techniques.

The alkyl 2-amino-2-(furan-2-yl)acetate hydrohalide salt of Formula B may be prepared by the two chemical processes shown in Scheme 1. In Path A, 2-(furan-2-yl)-2-oxoacetic acid (Formula C) is first converted into the O-alkyl oxime ester of Formula E (chemical steps a and b), as described in *Chemical Research in Toxicology*, 24(5) 706-717 (2011) and in *PCT Int. Application* 2005111001 (2005), and then E is converted into the halide salt of Formula B (chemical steps c and d). In Path B, the alkyl 2-methoxy-2-(N-carboxyalkylamino)acetate of two to about six molar equivalents of the base may be used in this reaction. Suitable bases include trialkylamines, alkali metal carbonates such as sodium carbonate or potassium carbonate, and the like. Suitable solvents include alcohols such as methanol, ethanol or 2-propanol. The present reaction is typically conducted with agitation sufficient to maintain an essentially uniform mixture of the reactants and generally requires from about 1 to about 10 hours, preferably

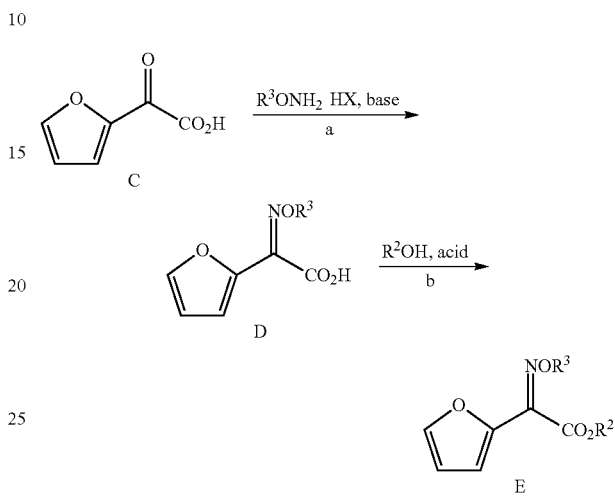

from about 1 to about 5 hours, to proceed to completion. The reaction is usually conducted at between about 25° C. and about 85° C., preferably between about 45° C. and about 65° C. After the reaction is complete, the oxime acid of Formula D is recovered by employing standard isolation and purification techniques.

The O-alkyl oxime acid of Formula D is then converted into the ester of Formula E by esterification in an alcohol solvent in the presence of an acid or an acid-forming compound. Suitable alcohol solvents include $C_1$-$C_4$ alcohols such as, for example, methanol, ethanol, 1-propanol and 1-butanol. Suitable acids include strong acids such as anhydrous hydrochloric acid, sulfuric acid or p-toluenesulfonic acid, and suitable acid-forming compounds include carboxylic acid halides such as acetyl chloride, acetyl bromide, propionyl chloride or propionyl bromide, and the like. From 0.01 to

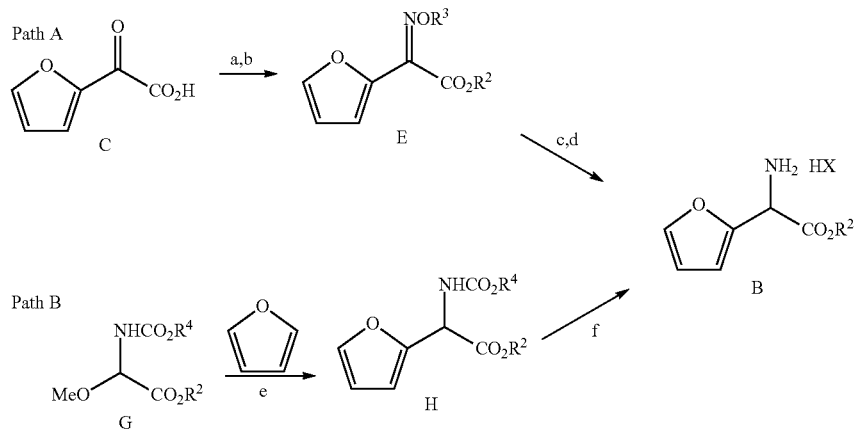

Formula G is coupled with furan, as described in *Bioorganic and Medicinal Chemistry*, 20(11), 3551-3564 (2012), to produce the 2-substituted furan of Formula H (chemical step e) which is then converted into the halide salt of Formula B (chemical step f).

A. Preparation of Compound of Formula B—Path A

The O-alkyl oxime ester of Formula E is prepared (chemical steps a and b) by first combining together an O-alkyl-hydroxylamine hydrohalide salt, 2-(furan-2-yl)-2-oxoacetic acid (Formula C), a base and a solvent, and heating the resulting mixture to produce the oxime acid of Formula D. From one to about three molar equivalents of the O-alkyl-hydroxylamine hydrohalide salt ($R^3$ is a $C_1$-$C_4$ alkyl) and from about about 2.0 molar equivalents of the acid or acid forming compound may be used. The reaction is usually conducted at between about 25° C. and about 85° C., preferably between about 45° C. and about 65° C. for a period of about 8 to about 48 hours, preferably for about 12 to about 24 hours. After the reaction is complete, the oxime ester of Formula E is recovered by employing standard isolation and purification techniques.

The O-alkyl oxime ester of Formula E is then converted to the aminoester of Formula F by reduction with zinc dust (chemical step c). This reaction is normally conducted in an alcohol solvent containing 50% aqueous formic acid. Suitable volume ratios of the alcohol solvent to the 50% aqueous formic acid are from about 4:1 to about 1:1, preferably from about 2:1 to about 1:1. Suitable alcohol solvents include $C_1$-$C_4$ alcohols such as, for example, methanol, ethanol, 1-propanol and 1-butanol, preferably, methanol may be used. From about 2 to about 4 molar equivalents of zinc dust are normally used and the reduction is normally run at 0-10° C. for 0.5 to about 2 hours and then at room temperature for about 12 to about 48 hours. After the reaction is complete, the aminoester F is recovered by employing standard isolation and purification techniques.

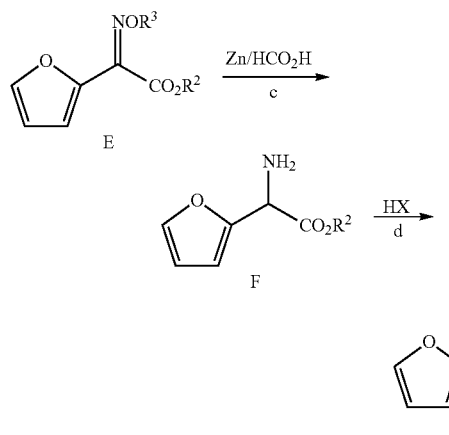

Aminoester F is then converted to the halide salt of Formula B by treatment with a strong acid such as hydrochloric acid, hydrobromic acid or sulfuric acid. From about 2 to about 6 molar equivalents of the strong acid may be used and may be added to a solution of aminoester F in a water immiscible solvent such as diethyl ether, methyl t-butyl ether, 2-methyl furan, dioxane, and the like. The strong acid is normally used in an anhydrous form such as a solution in a non-aqueous solvent such as, for example, acetic acid or dioxane. The strong acid may also be added to the process in the form of a gas or a neat liquid. The strong acid is normally added to aminoester F at from about 0° C. to about room temperature, and the resulting mixture then conducted for about 0.5 to about 2.0 hours at room temperature. The halide salt B is recovered by employing standard isolation and purification techniques.

B. Preparation of Compound of Formula B—Path B

Utilizing Path B (Scheme 1), the 2-methoxyaminoacid derivative of Formula G is coupled with furan in the presence of a Lewis acid to provide the 2-substituted furan of Formula H. The compound of Formula G, wherein $R^2$ is a $C_1$-$C_4$ alkyl and $R^4$ is an acid cleavable group selected from allyl, benzyl or a substituted allyl or benzyl group, is placed in a solvent and then treated at room temperature with the Lewis acid, followed immediately by the addition of furan. Suitable solvents for use in this reaction include diethyl ether, methyl t-butyl ether, 2-methyl furan, dioxane, and the like. Suitable Lewis acids include boron trifluoride etherate, aluminum trichloride, tin tetrachloride, and the like. Relative to compound G, from about 1.0-2.0, preferably from about 1.2-1.7, molar equivalents of the Lewis acid and from about 2.0-6.0, preferably from about 3.0-5.0, molar equivalents of furan are typically used in this coupling reaction. The reaction is typically conducted for about 10 hours to about 48 hours, preferably for about 18 to about 32 hours at room temperature. After the reaction is complete, the 2-substituted furan of Formula H is recovered by employing standard isolation and purification techniques.

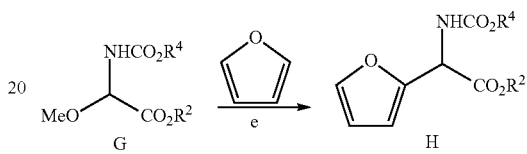

The compound of Formula H is converted to the compound of Formula B by treatment with a strong acid, such as, hydrochloric acid, hydrobromic acid or sulfuric acid, at room temperature in a polar, carboxylic acid solvent such as acetic acid, propionic acid, and the like. From about 2.0 to about 7.0, preferably from about 4.0 to about 6.0, molar equivalents of the strong acid may be used. The reaction is conducted for about 0.25 to about 5.0 hours, preferably for about 0.5 to about 2 hours at room temperature. After the reaction is complete, the 2-substituted furan of Formula B is recovered by employing standard isolation and purification techniques.

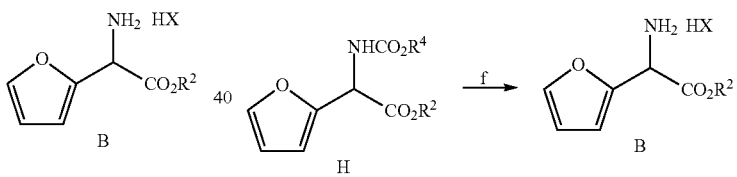

The following examples are presented to illustrate the disclosure.

EXAMPLES

Example 1a

Methyl 4,6-dibromo-3-hydroxypicolinate

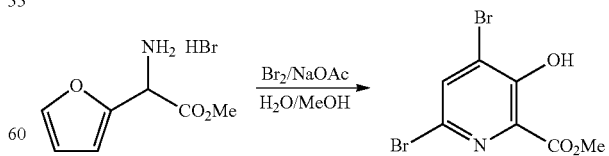

To a magnetically stirred solution of methyl 2-amino-2-(furan-2-yl)acetate hydrobromide (0.84 g, 3.56 mmol) and sodium acetate (1.255 g, 15.30 mmol) in 40 mL of water at 0° C. was added dropwise a solution of bromine (0.788 ml, 15.30 mmol) in 10 mL of MeOH over 30 min. After warming to room temperature for 24 hr, the reaction mixture was filtered through a fritted glass funnel and the white solid was washed with water. Solvent removal gave methyl 4,6-dibromo-3-hydroxypicolinate (577 mg, 1.837 mmol, 51.6% yield) as a white solid; Mp 180-181° C. (recrystallized from heptane). $^1$H NMR (600 MHz, Chloroform-d) δ 11.35 (s, 1H), 7.86 (s, 1H), 4.07 (s, 3H); $^{13}$C NMR (151 MHz, Chloroform-d) δ 168.74, 156.02, 136.85, 130.14, 129.92, 124.67, 53.84. HRMS-ESI (m/z) calc'd for $[C_7H_5Br_2NO_3]^+$, 308.8636. found, 308.8638.

Example 1b

Methyl 4,6-dibromo-3-hydroxypicolinate

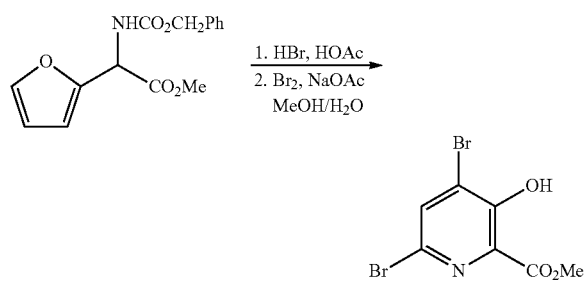

To magnetically stirred 33 wt % hydrogen bromide (10.00 ml, 55.2 mmol) in acetic acid was added methyl 2-(((benzyloxy)carbonyl)amino)-2-(furan-2-yl)acetate (2.89 g, 10 mmol). After stirring at room temperature for 1 hr, 150 mL of anhydrous ether was added to give 2.34 g of a grey solid. To a magnetically stirred solution of this grey solid and sodium acetate (3.53 g, 43.0 mmol) in 100 mL of water at 0° C. was added dropwise of a solution of bromine (2.215 ml, 43.0 mmol) in 20 mL of MeOH. over 30 min. After stirring at room temperature, the reaction mixture was filtered through a fritted glass funnel. The off-white solid was dissolved in 75 mL of $CH_2Cl_2$, washed with 5 ml of a saturated aqueous solution of $Na_2S_2O_3$ and 5 mL of a saturated aqueous solution of NaCl, and dried ($MgSO_4$). Solvent removal gave methyl 4,6-dibromo-3-hydroxypicolinate (1.43 g, 4.32 mmol, 43.2% yield) as an off-white solid; Mp 179-180° C. (recrystallized from heptane). $^1$H NMR (400 MHz, Chloroform-d) δ 11.36 (d, J=0.4 Hz, 1H), 7.86 (m, 1H), 4.07 (s, 3H).

Example 2a 2-(Furan-2-yl)-2-(methoxyimino)acetic acid

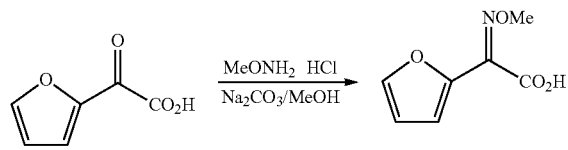

A magnetically stirred mixture of 2-(furan-2-yl)-2-oxoacetic acid (5.0 g, 35.7 mmol), O-methylhydroxylamine hydrochloride (5.96 g, 71.4 mmol) and $Na_2CO_3$ (15.13 g, 143 mmol) in 100 mL of MeOH was refluxed for 2 hr. The reaction mixture was cooled to room temperature and concentrated HCl was added slowly until a pH of 2-3 was obtained. Most of the solvent was removed on the rotary evaporator and the residue was diluted with 50 mL of water and 100 mL of ether. Concentrated HCl was again added to give a pH of 2-3. The aqueous layer was extracted with 2×50 mL of ether. The combined organic layers were washed with 50 mL of a saturated solution of NaCl, dried ($MgSO_4$) and solvent removed to give 6.58 g of crude 2-(furan-2-yl)-2-(methoxyimino)acetic acid as a viscous oil (crystals formed upon standing).

Example 2b

Methyl 2-(furan-2-yl)-2-(methoxyimino)acetate

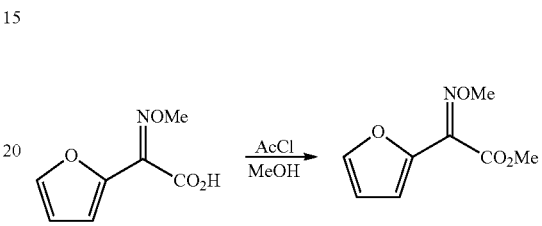

The crude 2-(furan-2-yl)-2-(methoxyimino)acetic acid (Example 2a) was dissolved in 100 mL of MeOH and was added to a solution of acetyl chloride (3.82 ml, 53.5 mmol) in 50 mL of MeOH. After refluxing for 16 hr, solvent was removed on the rotary evaporator and the crude product was added to 100 mL EtOAc and 20 mL of water. The organic layer was washed with 20 mL of a saturated solution of NaCl, dried ($MgSO_4$) and solvent removed to give methyl 2-(furan-2-yl)-2-(methoxyimino)acetate (6.35 g, 32.9 mmol, 92% yield) as a yellow oil. The product is a 4:1 mixture of isomers by H NMR. Major Isomer: $^1$H NMR (400 MHz, Chloroform-d) δ 7.53 (dd, J=1.7, 0.6 Hz, 1H). 7.31 (dd, J=3.5, 0.6 Hz, 1H), 6.54 (dd, J=3.5, 1.8 Hz, 1H), 4.15 (s, 3H), 3.94 (s, 3H); $^{13}$C NMR (101 MHz, Chloroform-d) δ 162.77, 144.82, 143.80, 142.47, 119.34, 111.78, 63.95, 53.10. HRMS-ESI (m/z) calc'd for $[C_8H_9NO_4]^+$, 183.0532. found, 183.0539.

Example 2c

Methyl 2-amino-2-(furan-2-yl)acetate

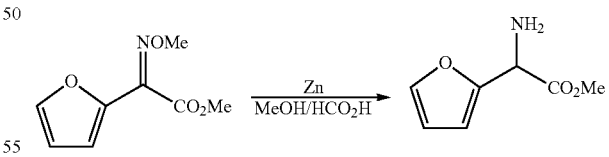

To a magnetically stirred solution of methyl 2-(furan-2-yl)-2-(methoxyimino)acetate (17.50 g, 96 mmol) in 300 mL of MeOH was added 200 mL of a solution of 50% formic acid in water. The reaction mixture was cooled to 0° C. (ice bath) and zinc dust (18.74 g, 287 mmol) was added. After stirring at room temperature for 18 hr, the reaction mixture was filtered through a plug of Celite and the plug was washed with MeOH. Solvent was removed on the rotary evaporator and the yellow residue was dissolved in 50 mL of water, basified to pH 10 with a saturated solution of $Na_2CO_3$ and extracted with 3×100 mL of EtOAc. After drying (MgSO$_4$) the organic extracts, solvent removal gave 10.2 g of methyl 2-amino-2-(furan-2-yl)acetate as an orange liquid.

Example 2d

Methyl 2-amino-2-(furan-2-yl)acetate hydrobromide

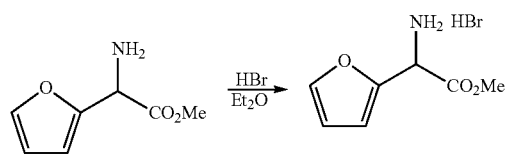 [SMILES: "Et2O" ; Br ; COC(=O)C(N)c1ccco1 ; Br ; COC(=O)C(N)c1ccco1]

The crude methyl 2-amino-2-(furan-2-yl)acetate (Example 2c) was dissolved in 350 mL of anhydrous ether and with rapid magnetic stirring, 10 mL of 33% wt HBr in acetic acid was added slowly by syringe. After stirring for 30 min, filtration followed by air drying gave methyl 2-amino-2-(furan-2-yl)acetate hydrobromide (12.35 g, 51.8 mmol, 54.2% yield) as an off-white solid; Mp 141-142° C. $^1$H NMR (400 MHz, DMSO-d6) δ 8.84 (s, 2H), 7.81 (dd, J=1.8, 0.7 Hz, 1H), 5.68 (d. J=3.3 Hz, 1H), 6.56 (dd, =3.3, 1.9 Hz, 1H), 5.59 (s, 1H), 3.77 (s, 3H); $^{13}$C NMR (151 MHz, DMSO-d6) δ 167.44, 145.49, 145.06, 112.14, 111.70, 53.98, 49.73.

Example 2e

Methyl 2-(((benzyloxy)carbonyl)amino)-2-(furan-2-yl)acetate

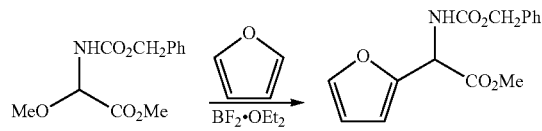

To a magnetically stirred solution of methyl 2-(((benzyloxy)carbonyl)amino)-2-methoxyacetate (10.89 g, 43 mmol) in 100 mL of anhydrous ether at room temperature under nitrogen was added boron trifluoride etherate (8.72 ml, 68.8 mmol) followed by the dropwise addition of furan (12.51 ml, 172 mmol) over 2 min. After stirring at room temperature for 24 hr, the reaction mixture was slowly added to 100 mL of a cold, saturated, aqueous solution of NaHCO$_3$. The mixture was extracted with 3×50 mL of EtOAc, and the combined organic layers were washed with a saturated solution of NaCl, dried (MgSO$_4$) and solvent removed to give 12.7 g of a colorless oil. Column chromatography on silica gel eluting with 20% EtOAc/hexane gave methyl 2-(((benzyloxy)carbonyl)amino)-2-(furan-2-yl)acetate (9.75 g, 33.0 mmol, 77% yield) as a white solid; Mp 80-81° C. $^1$H NMR (600 MHz, Chloroform-d) δ 7.35 (m, 6H), 6.35 (m, 2H), 5.77 (d, J=7.4 Hz, 1H), 5.54 (d, J=8.2 Hz, 1H), 5.12 (d, J=2.9 Hz, 2H), 3.77 (s, 3H); $^{13}$C NMR (151 MHz, Chloroform-d) δ 169.30, 155.43, 148.62, 142.92, 136.03, 128.54, 128.25, 128.16, 110.69, 108.64, 67.28, 53.08, 51.97. HRMS-ESI (m/z) calc'd for [C$_{15}$H$_{15}$NO$_5$]$^+$, 289.0950. found, 289.0942.

Example 2f

Methyl 2-amino-2-(furan-2-yl)acetate hydrobromide

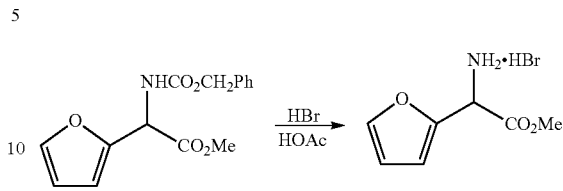

To magnetically stirred 33 wt % hydrogen bromide (2.00 ml, 11.04 mmol) in acetic acid was added methyl 2-(((benzyloxy)carbonyl)amino)-2-(furan-2-yl)acetate (579 mg, 2 mmol). After stirring at room temperature for 1 hr, 25 mL of anhydrous ether was added to give methyl 2-amino-2-(furan-2-yl)acetate hydrobromide (468 mg, 1.983 mmol, 99% yield) as a grey solid. $^1$H NMR (400 MHz, DMSO-d6) δ 8.93 (s, 2H), 7.81 (dd, J=1.8, 0.8 Hz, 1H), 6.69 (m, 1H), 6.57 (dd, J=3.3, 1.9 Hz, 1H), 5.61 (s, 1H), 3.78 (s, 3H).

What is claimed is:

1. A process for the preparation of the compound of Formula A

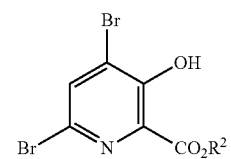

wherein R$^2$ is a C$_1$-C$_4$ alkyl;
which comprises the following steps:
a) creating a mixture by adding a brominating agent and water to the compound of Formula B

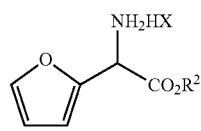

wherein X is Cl or Br, and R$^2$ is a C$_1$-C$_4$ alkyl; and
b) isolating the compound of Formula A from the mixture.
2. The process of claim 1 wherein the brominating agent is bromine.
3. The process of claim 1 further including a base.
4. A process for the preparation of the compound of Formula B

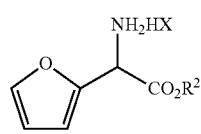

wherein X is Cl or Br, and R$^2$ is a C$_1$-C$_4$ alkyl;
which comprises the following steps:
a) creating a first mixture by combining together an O-alkylhydroxylamine hydrohalide salt of Formula I, a base, and a compound of Formula C and heating the first mixture

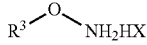

wherein X is Cl or Br, and $R^3$ is a $C_1$-$C_4$ alkyl;

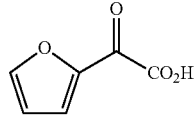

b) isolating a compound of Formula D from the first mixture

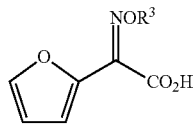

wherein $R^3$ is a $C_1$-$C_4$ alkyl;
c) mixing a compound of Formula D with an alcohol and an acid compound or acid forming compound and heating to form a second mixture;
d) isolating a compound of Formula E from the second mixture

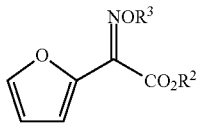

wherein $R^2$ and $R^3$ are independently a $C_1$-$C_4$ alkyl;
e) adding a reducing agent to the compound of Formula E to form a third mixture;
f) isolating a compound of Formula F from the third mixture

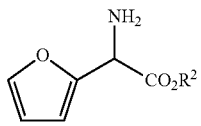

wherein $R^2$ is a $C_1$-$C_4$ alkyl;
g) adding a hydrohalide acid to the compound of Formula F to form a fourth mixture; and
h) isolating the compound of Formula B from the fourth mixture.

5. The process of claim 4 wherein the reducing agent is zinc metal.
6. The process of claim 4 wherein the hydrohalide acid is selected from hydrochloric acid and hydrobromic acid.
7. A process for the preparation of the compound of Formula B

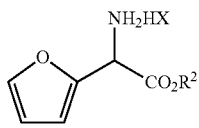

wherein X is Cl or Br, and $R^2$ is a $C_1$-$C_4$ alkyl;
which comprises the following steps:
a) creating a first mixture by combining together furan, a Lewis acid and a compound of Formula G

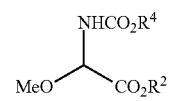

wherein $R^2$ is a $C_1$-$C_4$ alkyl and $R^4$ is an acid cleavable group selected from an allyl, a benzyl or a substituted allyl or benzyl group;
b) isolating a compound of Formula H from the first mixture

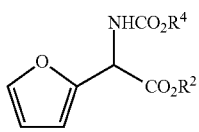

wherein $R^2$ and $R^4$ are as defined in step a);
c) adding a strong acid to the compound of Formula H to form a second mixture; and
d) isolating the compound of Formula B from the second mixture.
8. The process of claim 7 wherein the Lewis acid is boron trifluoride etherate.
9. The process of claim 7 wherein the acid cleavable group is a benzyl group.
10. The process of claim 7 wherein the strong acid is selected from hydrochloric acid and hydrobromic acid.
11. A compound consisting of:

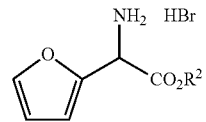

wherein $R^2$ is a $C_1$-$C_4$ alkyl.

* * * * *